United States Patent
Ledbetter

(10) Patent No.: US 11,747,413 B2
(45) Date of Patent: Sep. 5, 2023

(54) METHODS AND SYSTEMS FOR FAST FIELD ZEROING FOR MAGNETOENCEPHALOGRAPHY (MEG)

(71) Applicant: HI LLC, Los Angeles, CA (US)

(72) Inventor: Micah Ledbetter, Sunnyvale, CA (US)

(73) Assignee: HI LLC, Los Angeles, CA (US)

( * ) Notice: Subject to any disclaimer, the term of this patent is extended or adjusted under 35 U.S.C. 154(b) by 529 days.

(21) Appl. No.: 17/004,507

(22) Filed: Aug. 27, 2020

(65) Prior Publication Data

US 2021/0063510 A1  Mar. 4, 2021

Related U.S. Application Data

(60) Provisional application No. 62/960,548, filed on Jan. 13, 2020, provisional application No. 62/895,197, filed on Sep. 3, 2019.

(51) Int. Cl.
*G01R 33/26* (2006.01)
*A61B 5/245* (2021.01)
*A61B 5/00* (2006.01)

(52) U.S. Cl.
CPC .............. *G01R 33/26* (2013.01); *A61B 5/245* (2021.01); *A61B 5/6801* (2013.01);
(Continued)

(58) Field of Classification Search
None
See application file for complete search history.

(56) References Cited

U.S. PATENT DOCUMENTS

| | | |
|---|---|---|
| 3,173,082 A | 3/1965 | Bell et al. |
| 3,257,608 A | 6/1966 | Bell et al. |

(Continued)

FOREIGN PATENT DOCUMENTS

| | | |
|---|---|---|
| CN | 104730484 | 6/2015 |
| CN | 107562188 | 1/2018 |

(Continued)

OTHER PUBLICATIONS

Budker et al., "Optical Magnetometry"., Nature Physics 3 (4), Dec. 2006. (Year: 2006).*

(Continued)

*Primary Examiner* — Yi-Shan Yang
(74) *Attorney, Agent, or Firm* — Branch Partners PLLC; Bruce E. Black

(57) ABSTRACT

A method of operating an optically pumped magnetometer (OPM) includes directing a light beam through a vapor cell of the OPM including a vapor of atoms; applying RF excitation to cause spins of the atoms to precess; measuring a frequency of the precession; for each of a plurality of different axes relative to the vapor cell, directing a light beam through the vapor cell, applying a magnetic field through the vapor cell along the axis, applying RF excitation to cause spins of the atoms to precess, and measuring a frequency of the precession in the applied magnetic field; determining magnitude and components of an ambient background magnetic field along the axes using the measured frequencies; and applying a magnetic field based on the components around the vapor cell to counteract the ambient background magnetic field to facilitate operation of the OPM in a spin exchange relaxation free (SERF) mode.

20 Claims, 5 Drawing Sheets

(52) U.S. Cl.
CPC ... *A61B 2562/0223* (2013.01); *A61B 2562/04* (2013.01); *A61B 2562/06* (2013.01)

(56) References Cited

U.S. PATENT DOCUMENTS

| | | | |
|---|---|---|---|
| 3,495,161 | A | 2/1970 | Bell |
| 3,501,689 | A | 3/1970 | Robbiano |
| 3,513,381 | A | 5/1970 | Happer, Jr. |
| 4,193,029 | A | 3/1980 | Cioccio et al. |
| 4,951,674 | A | 8/1990 | Zanakis et al. |
| 5,189,368 | A | 2/1993 | Chase |
| 5,192,921 | A | 3/1993 | Chantry et al. |
| 5,225,778 | A | 7/1993 | Chaillout et al. |
| 5,254,947 | A | 10/1993 | Chaillout et al. |
| 5,309,095 | A | 5/1994 | Ahonen et al. |
| 5,442,289 | A | 8/1995 | Dilorio et al. |
| 5,444,372 | A | 8/1995 | Wikswo, Jr. et al. |
| 5,471,985 | A | 12/1995 | Warden |
| 5,506,200 | A | 4/1996 | Hirschkoff et al. |
| 5,526,811 | A | 6/1996 | Lypchuk |
| 5,713,354 | A | 2/1998 | Warden |
| 6,144,872 | A | 11/2000 | Graetz |
| 6,339,328 | B1 | 1/2002 | Keene et al. |
| 6,472,869 | B1 | 10/2002 | Upschulte et al. |
| 6,665,553 | B2 | 12/2003 | Kandori et al. |
| 6,806,784 | B2 | 10/2004 | Hollberg et al. |
| 6,831,522 | B2 | 12/2004 | Kitching et al. |
| 7,038,450 | B2 | 5/2006 | Romalis et al. |
| 7,102,451 | B2 | 9/2006 | Happer et al. |
| 7,145,333 | B2 | 12/2006 | Romalis et al. |
| 7,521,928 | B2 | 4/2009 | Romalis et al. |
| 7,656,154 | B2 | 2/2010 | Kawabata et al. |
| 7,826,065 | B1 * | 11/2010 | Okandan ............ G01R 33/032 356/521 |
| 7,872,473 | B2 | 1/2011 | Kitching et al. |
| 7,994,783 | B2 | 8/2011 | Ledbetter et al. |
| 8,054,074 | B2 | 11/2011 | Ichihara et al. |
| 8,212,556 | B1 | 7/2012 | Schwindt et al. |
| 8,258,884 | B2 | 9/2012 | Borwick, III et al. |
| 8,319,156 | B2 | 11/2012 | Borwick, III et al. |
| 8,334,690 | B2 | 12/2012 | Kitching et al. |
| 8,373,413 | B2 | 2/2013 | Sugioka |
| 8,405,389 | B2 | 3/2013 | Sugioka et al. |
| 8,587,304 | B2 | 11/2013 | Budker et al. |
| 8,836,327 | B2 | 9/2014 | French et al. |
| 8,906,470 | B2 | 12/2014 | Overstolz et al. |
| 8,941,377 | B2 | 1/2015 | Mizutani et al. |
| 9,084,549 | B2 | 7/2015 | Desain et al. |
| 9,095,266 | B1 | 8/2015 | Fu |
| 9,116,201 | B2 | 8/2015 | Shah et al. |
| 9,140,590 | B2 | 9/2015 | Waters et al. |
| 9,140,657 | B2 | 9/2015 | Ledbetter et al. |
| 9,169,974 | B2 | 10/2015 | Parsa et al. |
| 9,244,137 | B2 | 1/2016 | Kobayashi et al. |
| 9,291,508 | B1 | 3/2016 | Biedermann et al. |
| 9,343,447 | B2 | 3/2016 | Parsa et al. |
| 9,366,735 | B2 | 6/2016 | Kawabata et al. |
| 9,383,419 | B2 | 7/2016 | Mizutani et al. |
| 9,395,425 | B2 | 7/2016 | Diamond et al. |
| 9,417,293 | B2 | 8/2016 | Schaffer et al. |
| 9,429,918 | B2 | 8/2016 | Parsa et al. |
| 9,568,565 | B2 | 2/2017 | Parsa et al. |
| 9,575,144 | B2 | 2/2017 | Kornack et al. |
| 9,601,225 | B2 | 3/2017 | Parsa et al. |
| 9,638,768 | B2 | 5/2017 | Foley et al. |
| 9,639,062 | B2 | 5/2017 | Dyer et al. |
| 9,677,905 | B2 | 6/2017 | Waters et al. |
| 9,726,626 | B2 | 8/2017 | Smith et al. |
| 9,726,733 | B2 | 8/2017 | Smith et al. |
| 9,791,536 | B1 | 10/2017 | Alem et al. |
| 9,829,544 | B2 | 11/2017 | Bulatowicz |
| 9,846,054 | B2 | 12/2017 | Waters et al. |
| 9,851,418 | B2 | 12/2017 | Wolf et al. |
| 9,869,731 | B1 | 1/2018 | Hovde et al. |
| 9,915,711 | B2 | 3/2018 | Kornack et al. |
| 9,927,501 | B2 | 3/2018 | Kim et al. |
| 9,948,314 | B2 | 4/2018 | Dyer et al. |
| 9,964,609 | B2 | 5/2018 | Ichihara et al. |
| 9,964,610 | B2 | 5/2018 | Shah et al. |
| 9,970,999 | B2 | 5/2018 | Larsen et al. |
| 9,995,800 | B1 | 6/2018 | Schwindt et al. |
| 10,024,929 | B2 | 7/2018 | Parsa et al. |
| 10,088,535 | B1 | 10/2018 | Shah |
| 10,162,016 | B2 | 12/2018 | Gabrys et al. |
| 10,194,865 | B2 | 2/2019 | Le et al. |
| 10,314,508 | B2 | 6/2019 | Desain et al. |
| 10,371,764 | B2 | 8/2019 | Morales et al. |
| 10,772,561 | B2 | 9/2020 | Donaldson |
| 2004/0232912 | A1 | 11/2004 | Tsukamoto et al. |
| 2005/0007118 | A1 | 1/2005 | Kitching et al. |
| 2005/0046851 | A1 | 3/2005 | Riley, Jr. et al. |
| 2005/0206377 | A1 | 9/2005 | Romalis et al. |
| 2007/0076776 | A1 | 4/2007 | Lust et al. |
| 2007/0120563 | A1 | 5/2007 | Kawabata et al. |
| 2007/0167723 | A1 | 7/2007 | Park et al. |
| 2007/0205767 | A1 | 9/2007 | Xu et al. |
| 2009/0079426 | A1 | 3/2009 | Anderson |
| 2009/0101806 | A1 | 4/2009 | Masuda |
| 2010/0219820 | A1 | 9/2010 | Skidmore et al. |
| 2011/0062956 | A1 | 3/2011 | Edelstein et al. |
| 2012/0112749 | A1 | 5/2012 | Budker et al. |
| 2013/0082700 | A1 | 4/2013 | Mizutani et al. |
| 2013/0082701 | A1 | 4/2013 | Mizutani et al. |
| 2013/0265042 | A1 | 10/2013 | Kawabata et al. |
| 2014/0121491 | A1 | 5/2014 | Zhang |
| 2014/0159718 | A1 | 6/2014 | Larsen et al. |
| 2014/0306700 | A1 | 10/2014 | Kamada et al. |
| 2014/0354275 | A1 | 12/2014 | Sheng et al. |
| 2015/0022200 | A1 | 1/2015 | Ichihara et al. |
| 2015/0054504 | A1 | 2/2015 | Ichihara et al. |
| 2015/0378316 | A1 | 12/2015 | Parsa et al. |
| 2016/0061913 | A1 | 3/2016 | Kobayashi et al. |
| 2016/0116553 | A1 | 4/2016 | Kim et al. |
| 2016/0223627 | A1 | 8/2016 | Shah et al. |
| 2016/0291099 | A1 | 10/2016 | Ueno |
| 2016/0313417 | A1 | 10/2016 | Kawabata et al. |
| 2017/0023653 | A1 | 1/2017 | Kobayashi et al. |
| 2017/0023654 | A1 | 1/2017 | Kobayashi et al. |
| 2017/0067969 | A1 | 3/2017 | Butters et al. |
| 2017/0199138 | A1 | 7/2017 | Parsa et al. |
| 2017/0199251 | A1 | 7/2017 | Fujii et al. |
| 2017/0261564 | A1 | 9/2017 | Gabrys et al. |
| 2017/0293005 | A1 * | 10/2017 | Panther ............ G01R 33/445 |
| 2017/0331485 | A1 | 11/2017 | Gobet et al. |
| 2017/0343617 | A1 | 11/2017 | Manickam et al. |
| 2017/0343695 | A1 | 11/2017 | Stetson et al. |
| 2017/0356969 | A1 | 12/2017 | Ueno |
| 2017/0360322 | A1 | 12/2017 | Ueno |
| 2017/0363695 | A1 | 12/2017 | Ueno |
| 2018/0003777 | A1 | 1/2018 | Sorenson et al. |
| 2018/0038921 | A1 | 2/2018 | Parsa et al. |
| 2018/0100749 | A1 | 4/2018 | Waters et al. |
| 2018/0128885 | A1 | 5/2018 | Parsa et al. |
| 2018/0156875 | A1 | 6/2018 | Herbsommer et al. |
| 2018/0219353 | A1 | 8/2018 | Shah |
| 2018/0238974 | A1 | 8/2018 | Shah et al. |
| 2018/0275221 | A1 * | 9/2018 | Bruce ............ G01R 33/032 |
| 2018/0313908 | A1 | 11/2018 | Knappe et al. |
| 2018/0313913 | A1 | 11/2018 | DeNatale et al. |
| 2018/0372813 | A1 | 12/2018 | Bulatowicz et al. |
| 2019/0154769 | A1 | 5/2019 | Nagasaka et al. |
| 2019/0391213 | A1 | 12/2019 | Alford |
| 2020/0025844 | A1 | 1/2020 | Alford et al. |
| 2020/0057115 | A1 | 2/2020 | Jiménez-Martínez et al. |
| 2020/0057116 | A1 | 2/2020 | Zorzos et al. |
| 2020/0064421 | A1 | 2/2020 | Kobayashi et al. |
| 2020/0072916 | A1 | 3/2020 | Alford et al. |
| 2020/0088811 | A1 | 3/2020 | Mohseni |
| 2020/0241094 | A1 | 7/2020 | Alford |
| 2020/0256929 | A1 | 8/2020 | Ledbetter et al. |
| 2020/0309873 | A1 | 10/2020 | Ledbetter et al. |
| 2020/0334559 | A1 | 10/2020 | Anderson et al. |
| 2020/0341081 | A1 | 10/2020 | Mohseni et al. |
| 2020/0381128 | A1 | 12/2020 | Pratt et al. |

(56) References Cited

U.S. PATENT DOCUMENTS

| | | | |
|---|---|---|---|
| 2020/0400763 | A1 | 12/2020 | Pratt |
| 2021/0015427 | A1 | 1/2021 | Shah et al. |
| 2021/0080522 | A1* | 3/2021 | Alford .............. G01R 33/0017 |
| 2022/0011386 | A1* | 1/2022 | Knappe ............... G01R 33/032 |

FOREIGN PATENT DOCUMENTS

| | | |
|---|---|---|
| CN | 110742607 | 2/2020 |
| CN | 110859610 | 3/2020 |
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |
| WO | 2020/084194 | 4/2020 |

OTHER PUBLICATIONS

Fang et al., "In situ triaxial magnetic field compensation for the spin-exchange-relaxation-free atomic magnetometer" Review of Scientific Instrument. 83, 103104 (2012). (Year: 2012).*

Hill RM, Boto E, Holmes N, et al. A tool for functional brain imaging with lifespan compliance [published correction appears in Nat Commun. Dec. 4, 2019;10(1):5628]. Nat Commun. 2019;10(1):4785. Published Nov. 5, 2019. doi:10.1038/s41467-019-12486-x.

Zetter, R., Iivanainen, J. & Parkkonen, L. Optical Co-registration of MRI and On-scalp MEG. Sci Rep 9, 5490 (2019). https://doi.org/10.1038/s41598-019-41763-4.

Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.

Hill RM, Boto E, Rea M, et al. Multi-channel whole-head OPM-MEG: Helmet design and a comparison with a conventional system [published online ahead of print, May 29, 2020]. Neuroimage. 2020;219:116995. doi:10.1016/j.neuroimage.2020.116995.

V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.

Holmes, N., Tierney, T.M., Leggett, J. et al. Balanced, bi-planar magnetic field and field gradient coils for field compensation in wearable magnetoencephalography. Sci Rep 9, 14196 (2019).

N. Holmes, J. Leggett, E. Boto, G. Roberts, R.M. Hill, T.M. Tierney, V. Shah, G.R. Barnes, M.J. Brookes, R. Bowtell A bi-planar coil system for nulling background magnetic fields in scalp mounted magnetoencephalography Neuroimage, 181 (2018), pp. 760-774.

J. M. Leger et al., In-flight performance of the Absolute Scalar Magnetometer vector mode on board the Swarm satellites, Earth, Planets, and Space (2015) 67:57.

Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.

Gravrand, O., Khokhlov, A., & JL, L. M. (2001). On the calibration of a vectorial 4He pumped magnetometer. Earth, planets and space , 53 (10), 949-958.

Borna, Amir & Carter, Tony & Colombo, Anthony & Jau, Y-Y & Mckay, Jim & Weisend, Michael & Taulu, Samu & Stephen, Julia & Schwindt, Peter. (2018). Non-Invasive Functional-Brain-Imaging with a Novel Magnetoencephalography System. 9 Pages.

Vrba J, Robinson SE. Signal processing in magnetoencephalography. Methods. 2001;25(2):249-271. doi:10.1006/meth 2001.1238.

Uusitalo M and Ilmoniemi R., 1997, Signal-space projection method for separating MEG or EEG into components. Med. Biol. Comput. (35) 135-140.

Taulu S and Kajola M., 2005, Presentation of electromagnetic multichannel data: the signal space separation method. J. Appl. Phys. (97) 124905 (2005).

Taulu S, Simola J and Kajola M., 2005, Applications of the signal space separation method. IEEE Trans. Signal Process. (53) 3359-3372 (2005).

Taulu S, Simola J., 2006, Spatiotemporal signal space separation method for rejecting nearby interference in MEG measurements. Phys. Med. Biol. (51) 1759-1768 (2006).

Johnson, et al., Magnetoencephalography with a two-color pump-probe, fiber-coupled atomic magnetometer, Applied Physics Letters 97, 243703 2010.

Zhang, et al., Magnetoencephalography using a compact multichannel atomic magnetometer with pump-probe configuration, AIP Advances 8, 125028 (2018).

Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.

Ilmoniemi, R. (2009). The triangle phantom in magnetoencephalography. In 24th Annual Meeting of Japan Biomagnetism and Bioelecctromagnetics Society, Kanazawa, Japan, 28.29.5.2009 (pp. 6263).

Oyama D. Dry phantom for magnetoencephalography—Configuration, calibration, and contribution. J Neurosci Methods. 2015;251:24-36. doi: 0.1016/j.jneumeth.2015.05.004.

Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.

Eklund, E. Jesper, Andrei M. Shkel, Svenja Knappe, Elizabeth A. Donley and John Kitching. "Glass-blown spherical microcells for chip-scale atomic devices." (2008).

Jiménez-Martínez R, Kennedy DJ, Rosenbluh M, et al. Optical hyperpolarization and NMR detection of 129Xe on a microfluidic chip. Nat Commun. 2014;5:3908. Published May 20, 2014. doi: 10.1038/ncomms4908.

Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.

Bruno, A. C., and P. Costa Ribeiro. "Spatial Fourier Calibration Method for Multichannel Squid Magnetometers." Review of Scientific Instruments 62, No. 4 (Apr. 1, 1991): 1005-9.

Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.

Pasquarelli, A, M De Melis, Laura Marzetti, Hans-Peter Müller, and S N Erné. "Calibration of a Vector-MEG Helmet System." Neurology & Clinical Neurophysiology□: NCN 2004 (Feb. 1, 2004): 94.

Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." PLOS One 13, No. 5 (May 10, 2018): e0191111.

Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.

Nagel, S., & Spüler, M. (2019). Asynchronous non-invasive high-speed BCI speller with robust non-control state detection. Scientific Reports, 9(1), 8269.

Thielen, J., van den Broek, P., Farquhar, J., & Desain, P. (2015). Broad-Band Visually Evoked Potentials: Re(con)volution in Brain-Computer Interfacing. Plos One, 10(7), e0133797. https://doi.org/10.1371/journal.pone.0133797.

J. Kitching, "Chip-scale atomic devices," Appl. Phys. Rev. 5(3), 031302 (2018), 39 pages.

(56) References Cited

OTHER PUBLICATIONS

Arjen Stolk, Ana Todorovic, Jan-Mathijs Schoffelen, and Robert Oostenveld. "Online and offline tools for head movement compensation in MEG." Neuroimage 68 (2013): 39-48.
Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.
Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometrics, Inc., San Jose, CA, 95131, USA.
Pyragius, T., Marin Florez, H., & Fernholz, T. (2019). A Voigt effect based 3D vector magnetometer. Physical Review A, 100(2), https://doi.org/10.1103/PhysRevA.100.023416.
International Search Report and Written Opinion for PCT Application No. PCT/US2020/048129 dated Nov. 6, 2020.
Allred, J. C., Lyman, R. N., Kornack, T. W., & Romalis, M. V. (2002). High-sensitivity atomic magnetometer unaffected by spin-exchange relaxation. Physical review letters, 89(13), 130801.
Balabas et al. Polarized alkali vapor with minute-long transverse spin-relaxation time, Phys. Rev. Lett. 105, 070801—Published Aug. 12, 2010.
Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.
Dmitry Budker and Michael Romalis, "Optical Magnetometry," Nature Physics, 2008, https://arxiv.org/abs/physics/0611246v1.
Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).
Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.
Donley, E.A. & Hodby, E & Hollberg, L & Kitching, J. (2007). Demonstration of high-performance compact magnetic shields for chip-scale atomic devices. The Review of scientific instruments. 78. 083102.
Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.
Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10).ISSN 2331-7019.
Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.
Kiwoong Kim, Samo Begus, Hui Xia, Seung-Kyun Lee, Vojko Jazbinsek, Zvonko Trontelj, Michael V. Romalis, Multi-channel atomic magnetometer for magnetoencephalography: A configuration study. Neuroimage 89 (2014) 143-151 http://physics.princeton.edu/romalis/papers/Kim_2014.pdf.
Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2 49.
Kominis, I.K., Kornack, T.W., Allred, J.C. and Romalis, M.V., 2003. A subfemtotesla multichannel atomic magnetometer. Nature, 422(6932), p. 596.
Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi:10.1002/2016JA022389.
Lenz, J. and Edelstein, S., 2006. Magnetic sensors and their applications. IEEE Sensors journal, 6(3), pp. 631-649.
Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.
Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.
Sander TH, Preusser J, Mhaskar R, Kitching J, Trahms L, Knappe S. Magnetoencephalography with a chip-scale atomic magnetometer. Biomed Opt Express. 2012;3(5):981-90.
J. Seltzer, S & Romalis, Michael. (2010). High-temperature alkali vapor cells with antirelaxation surface coatings. Journal of Applied Physics. 106. 114905-114905. 10.1063/1.3236649.
Seltzer, S. J., and Romalis, M.V., "Unshielded three-axis vector operation of a spin-exchange-relaxation-free atomic magnetometer." Applied physics letters 85.20 (2004): 4804-4806.
Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.
Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.
Volkmar Schultze et al. An Optically Pumped Magnetometer Working in the Light-Shift Dispersed Mz Mode, Sensors 2017, 17, 561; doi:10.3390/s17030561.
Fang, J. and Qin, J., 2012. In situ triaxial magnetic field compensation for the spin-exchange-relaxation-free atomic magnetometer. Review of Scientific Instruments, 83(10), p. 103104.
Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.
Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.
Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.
Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.
Kim, Young Jin & Savukov, I. (2016). Ultra-sensitive Magnetic Microscopy with an Optically Pumped Magnetometer. Scientific Reports. 6. 24773. 10.1038/srep24773.
Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.
Orang Alem, Rahul Mhaskar, Ricardo Jimenez-Martinez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).
Slocum et al., Self-Calibrating Vector Magnetometer for Space, https://esto.nasa.gov/conferences/estc-2002/Papers/B3P4(Slocum).pdf.
Dupont-Roc, J & Haroche, S & Cohen-Tannoudji, C. (1969). Detection of very weak magnetic fields (10-9gauss) by 37Rb zero-field level crossing resonances. Physics Letters A—Phys Lett A. 28. 638-639. 10.1016/0375-9601(69)90480-0.

(56) References Cited

OTHER PUBLICATIONS

J. A. Neuman, P. Wang, and A. Gallagher, Robust high-temperature sapphire cell for metal vapors, Review of Scientific Instruments, vol. 66, Issue 4, Apr. 1995, pp. 3021-3023.
Borna, Amir, et al. "A 20-channel magnetoencephalography system based on optically pumped magnetometers." Physics in Medicine & Biology 62.23 (2017): 8909.
R. E. Slocum & L. J. Ryan, Design and operation of the minature vector laser magnetometer, Nasa Earth Science Technology Conference 2003.
Schoenmaker, Jeroen & R Pirota, K & Teixeira, Julio. (2013). Magnetic flux amplification by Lenz lenses. The Review of scientific instruments. 84. 085120. 10.1063/1.4819234.
Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.
Masuda, Y & Ino, T & Skoy, Vadim & Jones, G.L. (2005). 3He polarization via optical pumping in a birefringent cell. Applied Physics Letters. 87. 10.1063/1.2008370.
A.B. Baranga et al., An atomic magnetometer for brain activity imaging, Real Time Conference 2005. 14th IEEE-NPSS. pp. 417-418.
Larry J. Ryan, Robert E. Slocum, and Robert B. Steves, Miniature Vector Laser Magnetometer Measurements of Earth's Field, May 10, 2004, 4 pgs.
Lorenz, V. O., Dai, X., Green, H., Asnicar, T. R., & Cundiff, S. T. (2008). High-density, high-temperature alkali vapor cell. Review of Scientific Instruments, 79(12), 4 pages.
F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.
Huang, Haichao, et al. "Single-beam three-axis atomic magnetometer." Applied Physics Letters 109.6 (2016): 062404. (Year: 2016).
Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.
Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1. 2013), pp. 186-189.
Boto, E, Holmes, N, Leggett, J, Roberts, G, Shah, V, Meyer, SS, Muñoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.
Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific Instruments. 83. 113106. 10.1063/1.4766961.
Tierney, T. M., Holmes, N., Meyer, S. S., Boto, E., Roberts, G., Leggett, J., . . . Barnes, G. R. (2018). Cognitive neuroscience using wearable magnetometer arrays: Non-invasive assessment of language function. NeuroImage, 181, 513-520.
Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.
Zhang Xin et al: "Detection and analysis of MEG signals in occipital region with double channel OPM sensors", Journal of Neuroscience Methods, Elsevier Science Publisher B. V., Amsterdam, NL, vol. 346, Sep. 17, 2020 (Sep. 17, 2020).
Okada, Y.C., Lahteenmaki, A. and Xu, C., "Experimental analysis of distortion of magnetoencephalography signals by the skull." Clinical neurophysiology 110 (2), 230-238 (1999).
Robinson, J.T., Pohlmeyer, E., Gather, M.C., Kemere, C., Kitching, J.E., Malliaras, G.G., Marblestone, A., Shepard, K. L., Stieglitz, T. and Xie, C., "Developing Next-Generation Brain Sensing Technologies—A Review." IEEE sensors journal, 19(22), 10163-10175 (2019).
Shah, V., Knappe, S., Schwindt, P.D. and Kitching, J., "Subpicotesla atomic magnetometry with a microfabricated vapour cell." Nature Photon 1, 649-652 (2007).
Griffith, W.C., Knappe, S. and Kitching, J., "Femtotesla atomic magnetometry in a microfabricated vapor cell." Optics express 18, (26), 27167-27172 (2010).
Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).
Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).
Iivanainen, J., Stenroos, M. and Parkkonen, L., "Measuring MEG closer to the brain: Performance of on-scalp sensor arrays." NeuroImage 147, 542-553 (2017).
Kitching, J., Knappe, S., Gerginov, V., Shah, V., Schwindt, P.D., Lindseth, B., Donley E.A., "Chip-scale atomic devices: precision atomic instruments based on MEMS." In Frequency Standards And Metrology, 445-453 (2009).
Kitching, J., Knappe, S. and Donley, E.A., "Atomic sensors—a review." IEEE Sensors Journal, 11(9), 1749-1758 (2011).
Budker, D. and Romalis, M., "Optical magnetometry". Nature physics, 3(4), 227-234 (2007).
Happer, W., "Optical pumping", Rev. Mod. Phys., 44 (2), 169-249 (1972).
Purcell, E.M., Field, G.B., "Influence of collisions upon population of hyperfine states in hydrogen", Astrophys. J., 124, 542 (1956).
Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).
Bloom, A. L., "Principles of operation of the rubidium vapor magnetometer." Applied Optics 1(1), 61-68 (1962).
Bell, W.E., and Bloom, A.L., "Optically driven spin precession." Physical Review Letters 6, (6), 280 (1961).
Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).
Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).
De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).
Mellinger, J., Schalk, G., Braun, C., Preissl, H., Rosenstiel, W., Birbaumer, N. and Kübler, A., "An MEG-based brain-computer interface (BCI)." Neuroimage, 36(3), 581-593 (2007).
Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).
Lightfoot, G., "Summary of the N1-P2 cortical auditory evoked potential to estimate the auditory threshold in adults". Seminars in hearing, 37(1), 1 (2016).
Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).
Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).
Borna, A., Carter, T.R., Goldberg, J.D., Colombo, A.P., Jau, Y.Y., Berry, C., Mckay, J., Stephen, J., Weisend, M. and Schwindt, P.D.,

(56) References Cited

OTHER PUBLICATIONS

"A 20-channel magnetoencephalography system based on optically pumped magnetometers." Physics in Medicine & Biology, 62(23), 8909 (2017).

* cited by examiner

METHODS AND SYSTEMS FOR FAST FIELD ZEROING FOR MAGNETOENCEPHALOGRAPHY (MEG)

CROSS-REFERENCE TO RELATED APPLICATIONS

This application claims the benefit of U.S. Provisional Patent Applications Ser. Nos. 62/895,197, filed Sep. 3, 2019, and 62/960,548, filed Jan. 13, 2020, both of which are incorporated herein by reference in their entireties.

FIELD

The present disclosure is directed to the area of magnetic field measurement systems including systems for magnetoencephalography (MEG). The present disclosure is also directed to methods and systems for counteracting the ambient background magnetic field.

BACKGROUND

In the nervous system, neurons propagate signals via action potentials. These are brief electric currents which flow down the length of a neuron causing chemical transmitters to be released at a synapse. The time-varying electrical current within an ensemble of neurons generates a magnetic field. Magnetoencephalography (MEG), the measurement of magnetic fields generated by the brain, is one method for observing these neural signals.

Existing technology for measuring MEG typically utilizes superconducting quantum interference devices (SQUIDs) or collections of discrete optically pumped magnetometers (OPMs). SQUIDs require cryogenic cooling, which is bulky, expensive, requires a lot of maintenance. These requirements preclude their application to mobile or wearable devices.

An alternative to an array of SQUIDs is an array of OPMs. For MEG and other applications, the array of OPMS may have a large number of OPM sensors that are tightly packed. Such dense arrays can produce a high resolution spatial mapping of the magnetic field, and at a very high sensitivity level. Such OPMs sensors can be used for a wide range of applications, including sensing magnetic field generated by neural activities, similar to MEG systems.

BRIEF SUMMARY

One embodiment is a method of operating an optically pumped magnetometer (OPM) that includes directing a light beam through a vapor cell of the OPM including a vapor of atoms; applying RF excitation to the atoms to cause spins of the atoms of the vapor to precess; measuring a frequency of the precession by observing the light beam after passing through the vapor cell; for each of a plurality of different axes relative to the vapor cell, directing a light beam through the vapor cell, applying a magnetic field through the vapor cell along the axis, applying RF excitation to the atoms to cause spins of the atoms of the vapor to precess, and measuring a frequency of the precession in the applied magnetic field by observing the light beam after passing through the vapor cell; determining magnitude and components of an ambient background magnetic field along the axes using the measured frequencies; and applying a magnetic field based on the components around the vapor cell to counteract the ambient background magnetic field to facilitate operation of the OPM in a spin exchange relaxation free (SERF) mode.

Another embodiment is a magnetic field measurement system that includes an optically pumped magnetometer (OPM) having a vapor cell including a housing and a vapor of atoms disposed in the housing, a light source, a detector, and a magnetic field generator; and a processor coupled to the OPM and configured to perform actions including directing a light beam from the light source through the vapor cell of the OPM; applying RF excitation to the atoms to cause spins of the atoms of the vapor to precess; measuring a frequency of the precession by observing the light beam after passing through the vapor cell; for each of a plurality of different axes relative to the vapor cell, directing a light beam from the light source through the vapor cell, applying a magnetic field through the vapor cell along the axis, applying RF excitation to the atoms to cause spins of the atoms of the vapor to precess, and measuring a frequency of the precession in the applied magnetic field by observing the light beam after passing through the vapor cell; determining magnitude and components of an ambient background magnetic field along the axes using the measured frequencies; and applying a magnetic field based on the components around the vapor cell to counteract the ambient background magnetic field to facilitate operation of the OPM in a spin exchange relaxation free (SERF) mode.

In at least some embodiments, the plurality of different axes is three axes. In at least some embodiments, the three axes are three orthogonal axes.

In at least some embodiments, each instance of applying RF excitation includes applying RF excitation through an auxiliary coil of the OPM. In at least some embodiments, each instance of applying a magnetic field includes applying a magnetic field using a magnetic field generator of the OPM. In at least some embodiments, each instance of applying RF excitation includes applying RF excitation through the magnetic field generator of the OPM.

In at least some embodiments, each instance of directing a light beam includes generating a light beam using a laser of the OPM. In at least some embodiments, each instance of applying RF excitation includes applying RF excitation through one or more RF pulses. In at least some embodiments, each instance of applying RF excitation includes applying RF excitation by sweeping through an RF frequency range. In at least some embodiments, the atoms are alkali metal atoms.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
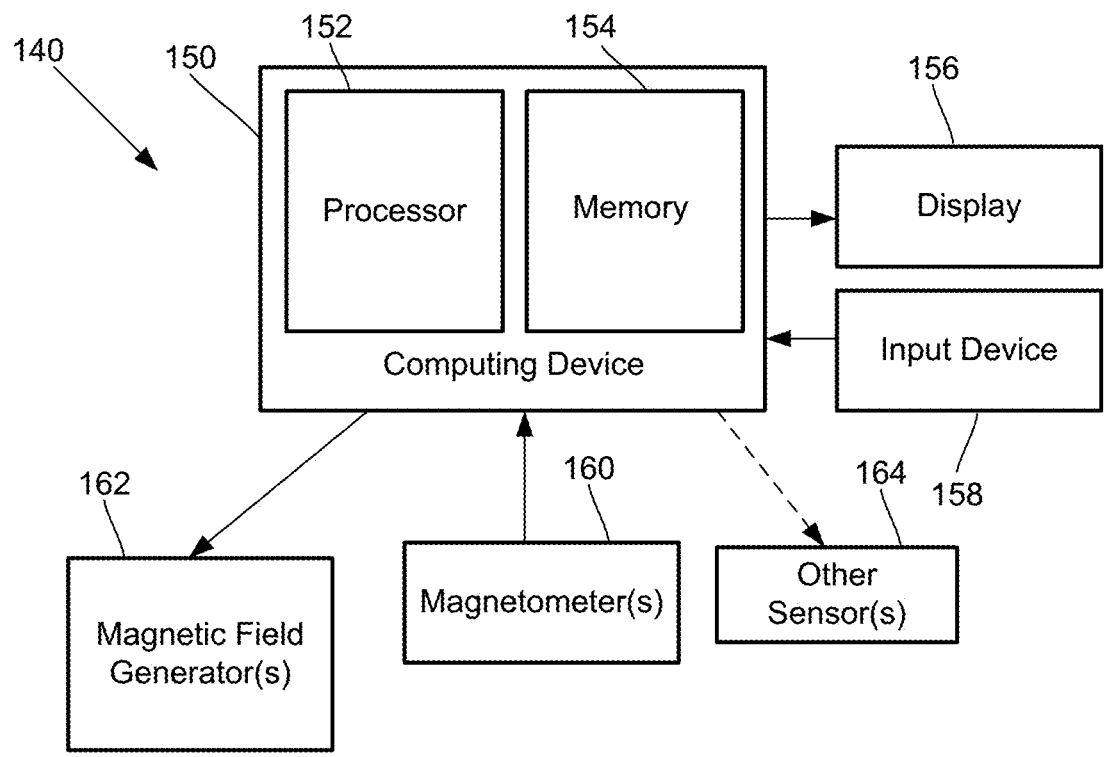
FIG. 1A is a schematic block diagram of one embodiment of a magnetic field measurement system, according to the invention.

The present disclosure is directed to the area of magnetic field measurement systems including systems for magnetoencephalography (MEG). The present disclosure is also directed to methods and systems for counteracting the ambient background magnetic field.

Herein the terms "ambient background magnetic field" and "background magnetic field" are interchangeable and used to identify the magnetic field or fields associated with sources other than the magnetic field measurement system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a vapor cell containing alkali metal vapor is described, but it will be recognized that other vapor cells can contain different gases or vapors for operation.

The methods and systems are described herein using optically pumped magnetometers (OPMs). While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems, such as a MEG system, described herein can be used to measure or observe electromagnetic signals generated by one or more magnetic field sources (for example, neural signals or other biological sources) of interest. The system can measure biologically generated magnetic fields and, at least in some embodiments, can measure biologically generated magnetic fields in a partially shielded environment. Aspects of a magnetic field measurement system will be exemplified below using magnetic signals from the brain of a user; however, biological signals from other areas of the body, as well as non-biological signals, can be measured using the system. In at least some embodiments, the system can be a wearable MEG system that can be portable and used outside a magnetically shielded room. A wearable MEG system will be used to exemplify the magnetic field measurement systems and calibration arrangements described herein; however, it will be recognized the calibration arrangements and methods described herein can be applied to other magnetic field measurement systems.

A magnetic field measurement system, such as a MEG system, can utilize one or more magnetic field sensors. Magnetometers will be used herein as an example of magnetic field sensors, but other magnetic field sensors may also be used in addition to, or as an alternative to, the magnetometers. FIG. 1A is a block diagram of components of one embodiment of a magnetic field measurement system 140 (such as a biological signal detection system.) The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions stored in the memory 154.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangement can also be used. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode.

Figure 1B:
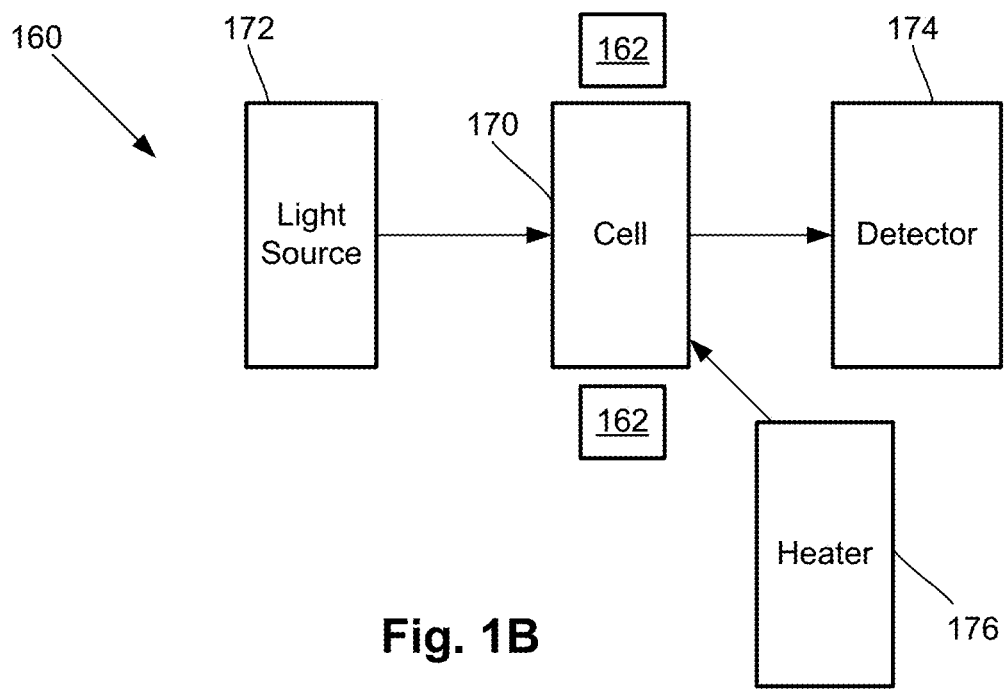
FIG. 1B is a schematic block diagram of one embodiment of a magnetometer, according to the invention.

FIG. 1B is a schematic block diagram of one embodiment of a magnetometer 160 which includes a vapor cell 170 (also referred to as a "cell") such as an alkali metal vapor cell; a heating device 176 to heat the cell 170; a light source 172; and a detector 174. In addition, coils of a magnetic field generator 162 can be positioned around the vapor cell 170. The vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and probe the vapor cell. The light source 172 may also include optics (such as lenses, waveplates, collimators, polarizers, and objects with reflective surfaces) for beam shaping and polarization control and for directing the light from the light source to the vapor cell 170 and detector 174. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
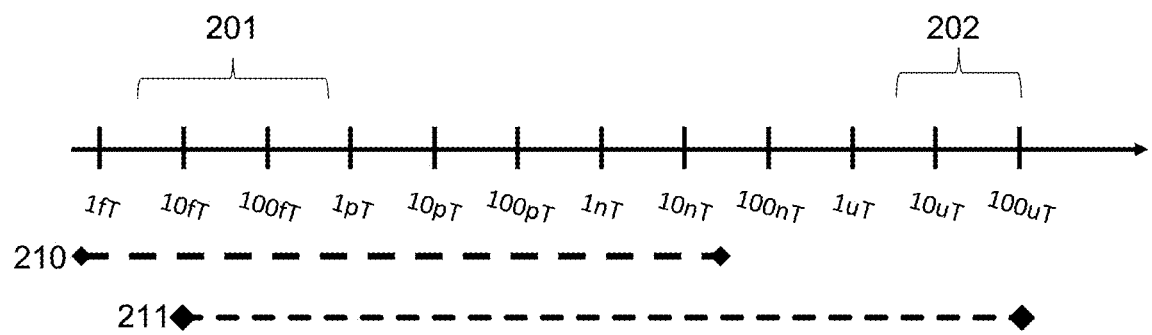
FIG. 2 shows a magnetic spectrum with lines indicating dynamic ranges of magnetometers operating in different modes.

FIG. 2 shows the magnetic spectrum from 1 f to 100 μT in magnetic field strength on a logarithmic scale. The magnitude of magnetic fields generated by the human brain are indicated by range 201 and the magnitude of the ambient background magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer but many conventional SERF magnetometers typically only operate up to about 0 to 200 nT while the scalar magnetometer starts in the 10 to 100 fT range but extends above 10 to 100 μT.

Superconducting quantum interference devices have been used to detect MEG signals; however such devices use expensive and immobile cryogenic dewars, making them unsuitable for portable/wearable MEG applications. Atomic magnetometers, and in particular SERF magnetometers, have been used for detecting MEG signals. However, SERF magnetometers utilize a near zero-magnetic field environment. Auxiliary solid state sensors can be employed to determine the ambient background magnetic field; however this can involve additional complexity and such sensors cannot measure the ambient background magnetic field at the location of the atoms. A method for determining the ambient background magnetic field rapidly using atomic signals is highly desirable.

Spin-exchange relaxation-free (SERF) atomic magnetometers operating at near zero magnetic field (to within approximately 50-100 nanoTesla) can be used to detect MEG signals. To operate in the ambient background magnetic field of the Earth (approximately 50 microTesla) some form of active or passive shielding (or a combination thereof) is used. In the case of active shielding, methods for rapidly determining the ambient background magnetic field at the magnetometer are highly beneficial. Presented herein are systems and methods to rapidly measure all three vector components of the ambient background magnetic field in order to rapidly counteract or reduce the ambient background magnetic field at the magnetometer without auxiliary sensors.

Figure 3:
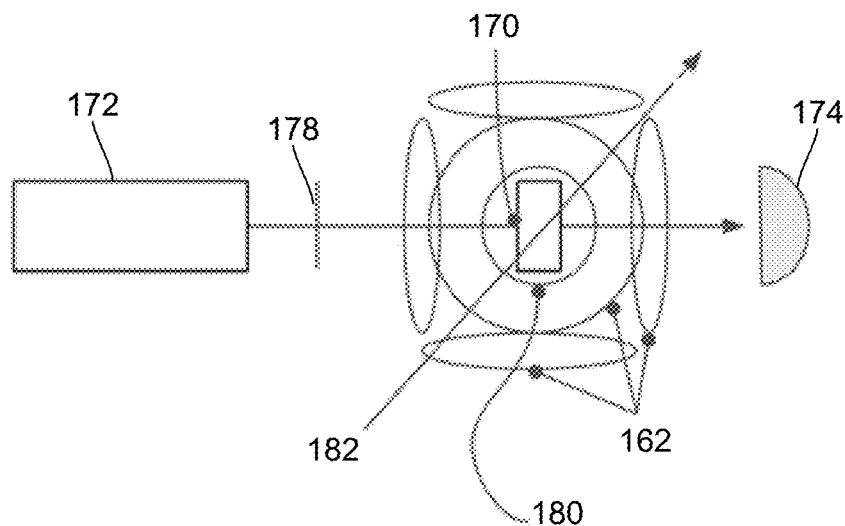
FIG. 3 is a schematic diagram is another embodiment of a magnetometer, according to the invention.

One embodiment of a system and method for quickly determining the ambient background magnetic field (for example, in at least some embodiments, making a determination within 5 milliseconds) is illustrated in FIG. 3. A light beam generated by a light source 172 (such as a laser) passes through a quarter-wave plate (QWP) 178 and a vapor cell 170. The intensity of the light is monitored with a detector 174 (such as a photodiode). The system operates in the ambient background magnetic field ($B_0$) (represented by arrow 182 in FIG. 3), which includes contributions from the Earth's dynamo and other man-made sources. A magnetic field generator 162 (for example, three sets of orthogonal compensation coils as illustrated in FIG. 3) can be used to apply magnetic fields to counteract or reduce the ambient background magnetic field in three orthogonal directions (e.g., x, y, and z directions). An optional auxiliary coil 180 can be used to apply RF excitation pulses, although in some embodiments, the RF excitation pulses can be applied using one or more of the coils of the magnetic field generator 162.

The light beam from the light source 172 is circularly polarized due to the quarter-wave plate 178 and optically pumps the alkali metal atoms of the vapor cell 170 in the direction of the light beam. Application of resonant RF magnetic field pulses with the excitation coil 180 induces the spins of the alkali metal atoms in the vapor cell 170 to precess at the Larmor precession frequency.

Figure 4:
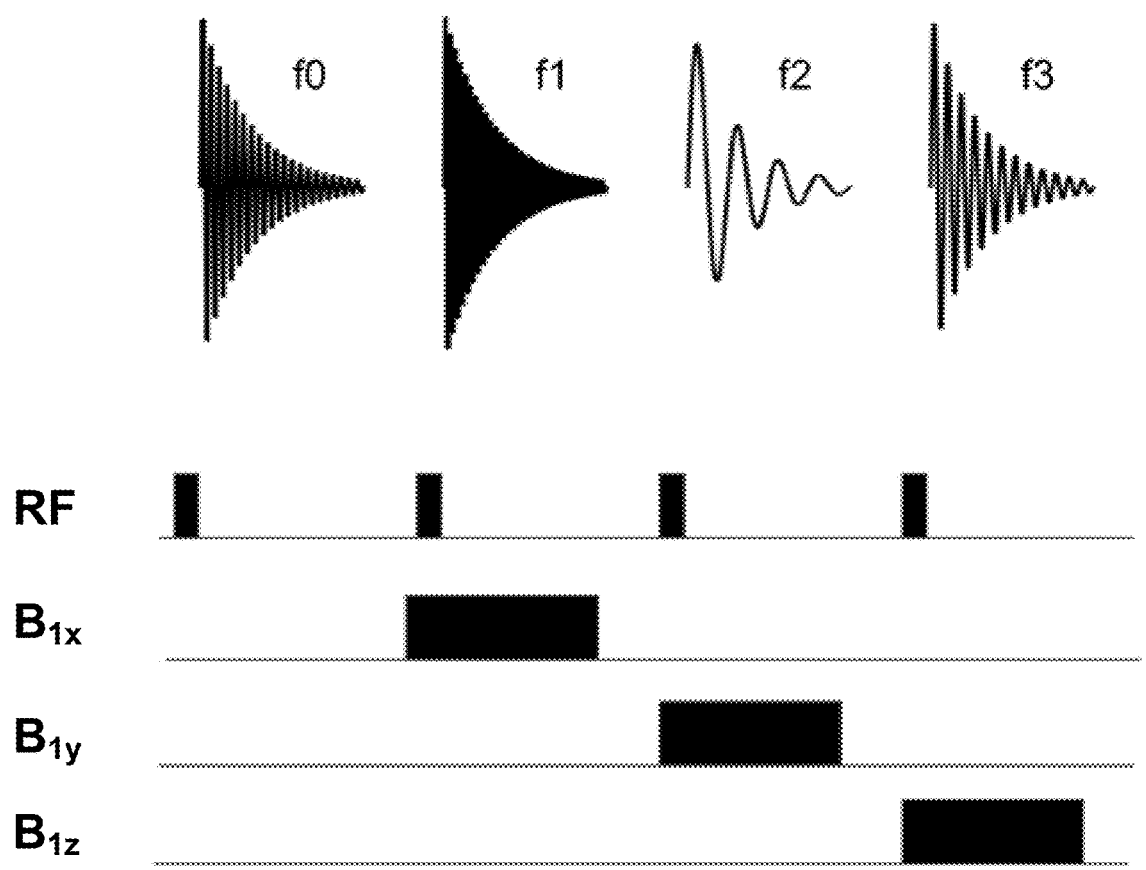
FIG. 4 is a schematic representation of the application of RF excitation and magnetic fields, along with the associated resulting free induction decay, to the magnetometer of FIG. 3, according to the invention.

One embodiment of a method to measure all three vector components of the magnetic field is illustrated in FIG. 4. An initial RF pulse 402 and subsequent free-induction decay 404 of the alkali metal spin polarization provides a measure of the magnitude of the ambient background magnetic field $B_0$ via the relation $f_0 = \gamma B_0$, where $\gamma$ is the gyro-magnetic ratio of the alkali metal atoms. To measure the frequency of spin precession, the free-induction decay can be fit to a sinusoid or Fourier-transformed. Any other suitable method can be used to determine the frequency. The precision of the measurement is approximately given by $\delta v = 1/SNR/(2\pi T_2^{3/2})$. In at least some embodiments, an estimated signal-to-noise ratio (SNR) of at least 100 is readily achievable and for $T_2 = 1$ ms, the uncertainty in the determination of frequency may be no more 50 Hz, corresponding to about 7 nT which indicates that the ambient background magnetic field can be reliably reduced so that a magnetometer using the vapor cell 170 can operate in SERF mode.

Returning to the method, three subsequent RF pulses 406, 408, 410 are individually applied along with small magnetic fields $B_{1x}$, $B_{1y}$, $B_{1z}$, respectively, from the different sets of orthogonal coils of the magnetic field generator 162, as illustrated in FIG. 4. The resulting free-induction decays 412, 414, 416 are observed. The precession frequencies $f_1$, $f_2$, $f_3$, respectively, yield a measure of the projection of the ambient background magnetic field along the three orthogonal axes as follows.

$$f_0 = \gamma B_0$$

$$f_1 = \gamma \sqrt{(B_0^2 + 2B_{1x}B_{0x} + B_{1x}^2)} \approx \gamma(B_0 + B_{1x}B_{0x}/B_0)$$

$$f_2 = \gamma \sqrt{(B_0^2 + 2B_{1y}B_{0y} + B_{1y}^2)} \approx \gamma(B_0 + B_{1y}B_{0y}/B_0)$$

$$f_3 = \gamma \sqrt{(B_0^2 + 2B_{1z}B_{0z} + B_{1z}^2)} \approx \gamma(B_0 + B_{1z}B_{0z}/B_0)$$

The approximate expressions on the right hand side of the above equations correspond to the first term in a Taylor expansion and are valid in the limit that $B_{1x}$, $B_{1y}$, $B_{1z}$ are small compared to $B_0$. Such approximations are convenient and likely to be valid but are not strictly necessary to enable reconstruction of the vector field components $B_{0x}$, $B_{0y}$, $B_{0z}$ of the ambient background magnetic field. Other approximations or calculations can be used to determine the vector field components of the ambient background magnetic field.

From measurements of precession frequencies, the vector field components $B_{0x}$, $B_{0y}$, $B_{0z}$ of the ambient background magnetic field can be estimated as follows:

$$B_{0x} = (f_1 - f_0)B_0/(\gamma B_{1x})$$

$$B_{0y} = (f_2 - f_0)B_0/(\gamma B_{1y})$$

$$B_{0z} = (f_3 - f_0)B_0/(\gamma B_{1z})$$

Knowledge of the vector field components enables the user or control system to rapidly find the magnetic field components for the magnetic field generator 162 to generate zero field (or near zero field) to enable operation of the magnetometer 160 in the SERF mode.

Figure 5:
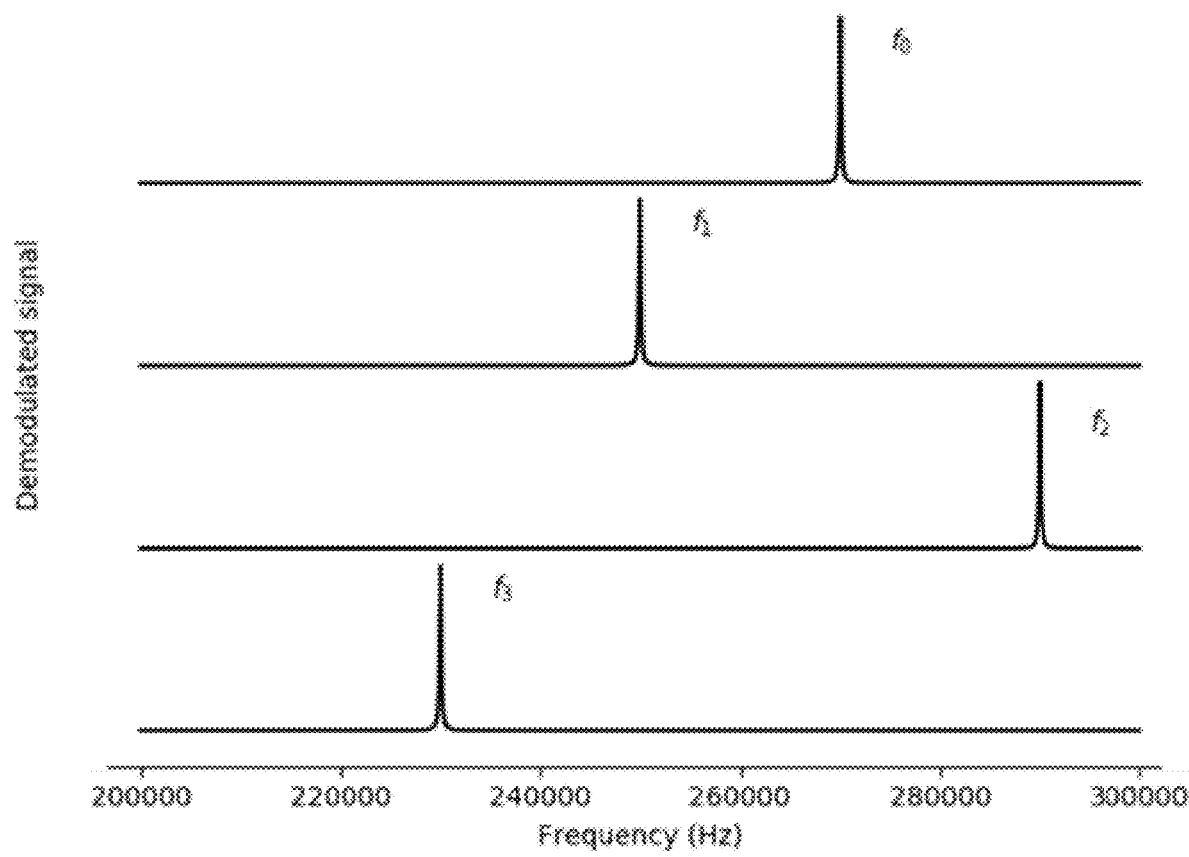
FIG. 5 is a schematic display of demodulated signals versus frequency arising from operation of the magnetometer of FIG. 3 with continuous-wave RF excitation sweeping through a Zeeman frequency of atoms of a vapor, according to the invention.

The method illustrated in FIG. 4 utilizes a pulsed RF field. An alternative implementation uses continuous wave RF excitation rather than pulsed RF excitation. In this case an RF magnetic field is swept across the ground state Zeeman resonance of the alkali metal atoms. The detector signal can be monitored via synchronous lock-in detection to find the location of the Zeeman resonance $f_0$. Subsequent continuous wave RF sweeps are performed in the presence of small applied magnetic fields in the x, y, and z directions, respectively, producing shifts in the frequency of the Zeeman resonance, as illustrated in FIG. 5. From here, finding the vector field components of the ambient background magnetic field is the same as the method illustrated in FIG. 4.

In at least some embodiments, the systems and methods described herein allow the use of atomic signals to rapidly measure all three vector field components of the ambient background magnetic field. In at least some embodiments, these methods and systems are fast when working in pulsed mode, and work in the ambient background magnetic field of the Earth.

Figure 6:
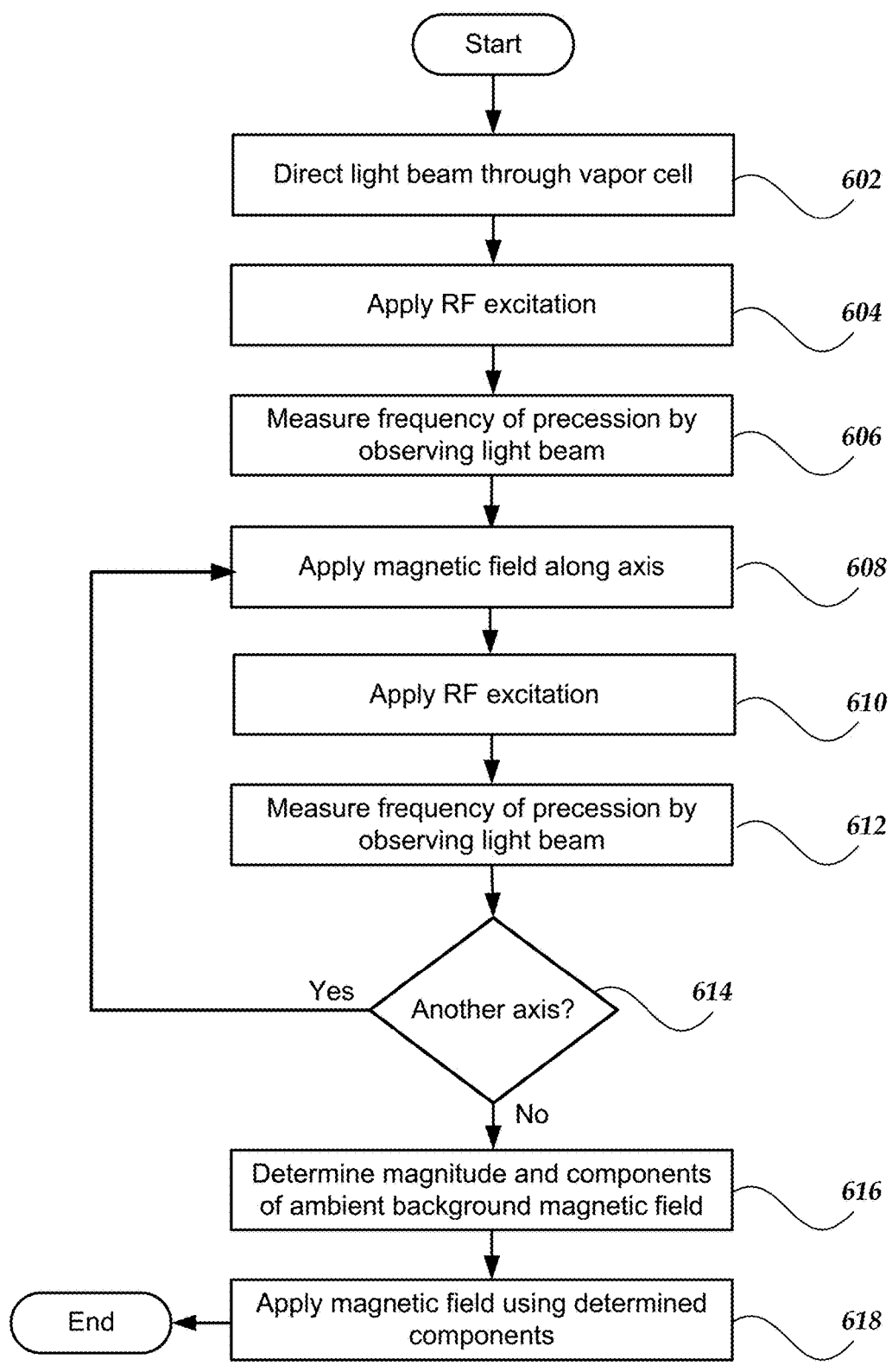
FIG. 6 is a flowchart of one embodiment of a method of operating an optically pumped magnetometer (OPM), according to the invention.

FIG. 6 illustrates one embodiment of a method of operating an optically pumped magnetometer (OPM) or a method of determining a magnitude and components of an ambient background magnetic field. In step 602, a light beam from a light source, such as a laser, is directed through a vapor cell of the OPM. The vapor cell includes a vapor of atoms, such as alkali metal atoms. The light beam pumps the atoms.

In step 604, an RF excitation is applied to the alkali metal atoms to cause spins of the atoms of the vapor to precess. The RF excitation can be a pulsed RF excitation, with sufficient bandwidth and a center frequency to excite the spins of the atoms of the vapor, or a continuous-wave RF excitation which sweeps through the Zeeman frequency of the atoms of the vapor. In at least some embodiments, the RF excitation can be applied through an auxiliary coil. In at least some embodiments, the RF excitation can be applied using a magnetic field generator of the OPM. In step 606, a frequency of the precession of the atoms of the vapor is measured by observing the light beam after passing through the vapor cell.

Steps 608 through 614 are individually performed for multiple different axes relative to the vapor cell. In at least some embodiments, the number of axes is three. In at least some embodiments, the axes are orthogonal to each other.

In step 608, a relatively small magnetic field, as compared to the ambient background magnetic field, is applied through the vapor cell along the axis while a light beam is directed through the vapor cell. This relatively small magnetic field can be applied using, for example, a magnetic field generator. In step 610, an RF excitation is applied to the alkali metal atoms to cause spins of the atoms of the vapor to precess similar to that applied in step 604. In step 612, a frequency of the precession in the applied magnetic field is measured by observing the light beam after passing through the vapor cell. In step 614, there is a determination if another axis is to be observed. If so, then the method proceeds back to step 608 using the next axis.

Using the measured frequencies, in step 616, the magnitude and vector field components of the ambient background magnetic field along the axes can be determined using the measured frequencies. In step 618, a magnetic field based on the vector field components can be applied around the vapor cell to counteract or reduce the ambient background magnetic field to facilitate operation of the OPM in a spin exchange relaxation free (SERF) mode.

Examples of magnetic field measurement systems in which the embodiments presented above can be incorporated, and which present features that can be incorporated in the embodiments presented herein, are described in U.S. Patent Application Publications Nos. 2020/0072916; 2020/0056263; 2020/0025844; 2020/0057116; 2019/0391213; 2020/0088811; 2020/0057115; 2020/0109481; 2020/0123416; and 2020/0191883; U.S. patent application Ser. Nos. 16/984,752; 16/984,720; 16/741,593; 16/752,393; 16/820,131; 16/850,380; 16/850,444; 16/884,672; 16/904,281; 16/922,898; and 16/928,810, and U.S. Provisional Patent Applications Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; 62/983,406; 63/031,469; and 63/037,407, all of which are incorporated herein by reference in their entireties.

The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A method of operating an optically pumped magnetometer (OPM), the method comprising:
    directing a first light beam through a vapor cell of the OPM comprising a vapor of atoms;
    while directing the first light beam through the vapor cell, applying radiofrequency (RF) excitation to the atoms to cause spins of the atoms of the vapor to precess;
    measuring a first frequency of the precession by observing the first light beam after passing through the vapor cell;
    determining a magnitude of an ambient background magnetic field from the first frequency;
    for each axis of a plurality of different axes relative to the vapor cell,
        directing another light beam through the vapor cell,
        applying a magnetic field through the vapor cell along the axis,
        while directing the other light beam through the vapor cell, applying RF excitation to the atoms to cause spins of the atoms of the vapor to precess,
        measuring another frequency of the precession in the applied magnetic field by observing the other light beam after passing through the vapor cell, and
        determining a vector field component of the ambient background magnetic field along the axis using the measured other frequency, the determined magnitude of the ambient background magnetic field, and a magnitude of the magnetic field applied along the axis; and
    applying a counteracting magnetic field, based on the determined vector field components of the ambient background magnetic field, around the vapor cell to counteract the ambient background magnetic field to facilitate operation of the OPM in a spin exchange relaxation free (SERF) mode.

2. The method of claim 1, wherein the plurality of different axes is three axes.

3. The method of claim 2, wherein the three axes are three orthogonal axes.

4. The method of claim 1, wherein each instance of applying RF excitation comprises applying RF excitation through an auxiliary coil of the OPM.

5. The method of claim 1, wherein each instance of applying a magnetic field comprises applying a magnetic field using a magnetic field generator of the OPM.

6. The method of claim 5, wherein each instance of applying RF excitation comprises applying RF excitation through the magnetic field generator of the OPM.

7. The method of claim 1, wherein each instance of directing a first light beam or directing another light beam comprises generating the first light beam or the other light beam, respectively, using a laser of the OPM.

8. The method of claim 1, wherein each instance of applying RF excitation comprises applying RF excitation through one or more RF pulses.

9. The method of claim 1, wherein each instance of applying RF excitation comprises applying RF excitation by sweeping through a frequency range.

10. The method of claim 1, wherein the atoms are alkali metal atoms.

11. A magnetic field measurement system, comprising:
an optically pumped magnetometer (OPM) comprising
a vapor cell comprising a housing and a vapor of atoms disposed in the housing,
a light source,
a detector, and
a magnetic field generator;
a memory having instructions stored thereon; and
a processor coupled to the OPM and the memory and configured execute the instructions to perform actions, the actions comprising
directing a first light beam through the vapor cell of the OPM;
while directing the first light beam through the vapor cell, applying radiofrequency (RF) excitation to the atoms to cause spins of the atoms of the vapor to precess;
measuring a first frequency of the precession by observing the first light beam after passing through the vapor cell;
determining a magnitude of an ambient background magnetic field from the first frequency;
for each axis of a plurality of different axes relative to the vapor cell,
directing another light beam through the vapor cell,
applying a magnetic field through the vapor cell along the axis,
while directing the other light beam through the vapor cell, applying RF excitation to the atoms to cause spins of the atoms of the vapor to precess,
measuring another frequency of the precession in the applied magnetic field by observing the other light beam after passing through the vapor cell, and
determining a vector field component of the ambient background magnetic field along the axis using the measured other frequency, the determined magnitude of the ambient background magnetic field, and a magnitude of the magnetic field applied along the axis; and
applying a counteracting magnetic field, based on the determined vector field components of the ambient background magnetic field, around the vapor cell to counteract the ambient background magnetic field to facilitate operation of the OPM in a spin exchange relaxation free (SERF) mode.

12. The magnetic field measurement system of claim 11, wherein the processor is configured so that the plurality of different axes is three axes.

13. The magnetic field measurement system of claim 11, wherein the processor is configured so that the three axes are three orthogonal axes.

14. The magnetic field measurement system of claim 11, wherein the processor is configured so that each instance of applying RF excitation comprises applying RF excitation through an auxiliary coil of the OPM.

15. The magnetic field measurement system of claim 11, wherein the processor is configured so that each instance of applying a magnetic field comprises applying a magnetic field using the magnetic field generator of the OPM.

16. The magnetic field measurement system of claim 15, wherein the processor is configured so that each instance of applying RF excitation comprises applying RF excitation through the magnetic field generator of the OPM.

17. The magnetic field measurement system of claim 11, wherein the processor is configured so that each instance of directing a first light beam or directing another light beam comprises generating the first light beam or the other light beam, respectively, using a laser of the OPM.

18. The magnetic field measurement system of claim 11, wherein the processor is configured so that each instance of applying RF excitation comprises applying RF excitation through one or more RF pulses.

19. The magnetic field measurement system of claim 11, wherein the processor is configured so that each instance of applying RF excitation comprises applying RF excitation by sweeping through an RF frequency range.

20. The magnetic field measurement system of claim 11, wherein the atoms are alkali metal atoms.

* * * * *